(12) United States Patent
Hasegawa (10) Patent No.: US 11,080,898 B2
(45) Date of Patent: Aug. 3, 2021

(54) ADAPTIVE PROCESSING OF MEDICAL IMAGES TO REDUCE NOISE MAGNITUDE

(71) Applicant: AlgoMedica, Inc., Sunnyvale, CA (US)

(72) Inventor: Akira Hasegawa, Chapel Hill, NC (US)

(73) Assignee: AlgoMedica, Inc., Sunnyvale, CA (US)

( * ) Notice: Subject to any disclaimer, the term of this patent is extended or adjusted under 35 U.S.C. 154(b) by 46 days.

(21) Appl. No.: 16/375,508

(22) Filed: Apr. 4, 2019

(65) Prior Publication Data

US 2019/0311507 A1    Oct. 10, 2019

Related U.S. Application Data (60) Provisional application No. 62/654,158, filed on Apr. 6, 2018.

(51) Int. Cl.
| | |
|---|---|
| *G06K 9/00* | (2006.01) |
| *G06T 11/00* | (2006.01) |
| *A61B 6/00* | (2006.01) |
| *A61B 6/03* | (2006.01) |

(52) U.S. Cl.
CPC ............ *G06T 11/008* (2013.01); *A61B 6/032* (2013.01); *A61B 6/5258* (2013.01); *G06T 2211/412* (2013.01)

(58) Field of Classification Search
None
See application file for complete search history.

(56) References Cited

U.S. PATENT DOCUMENTS

| | | | |
|---|---|---|---|
| 5,835,562 A | 11/1998 | Ramsdell et al. | |
| 7,245,755 B1 | 7/2007 | Pan et al. | |
| 2010/0272340 A1 | 10/2010 | Bar-Aviv et al. | |
| 2011/0110601 A1 | 5/2011 | Hong | |
| 2011/0286651 A1 | 11/2011 | Yu et al. | |
| 2012/0224760 A1* | 9/2012 | Goshen | G06T 5/002 382/131 |
| 2013/0051516 A1* | 2/2013 | Yang | A61B 6/5282 378/4 |
| 2013/0089247 A1 | 4/2013 | Mercuriev | |
| 2013/0202080 A1 | 8/2013 | Yu et al. | |

(Continued)

FOREIGN PATENT DOCUMENTS

WO    2017080847 A1    5/2017

OTHER PUBLICATIONS

Notification of Transmittal of the International Search Report and the Written Opinion of the International Searching Authority, or the Declaration dated Jun. 24, 2019 in connection with International Patent Application No. PCT/US2019/025777, 7 pages.

(Continued)

*Primary Examiner* — Wei Wen Yang (57) ABSTRACT

Each of a plurality of slices of medical image data is adaptively processed using a noise reduction mode selected according to a target noise magnitude for all slices to an estimated noise magnitude for the respective slice to obtain consistent processed images for across slices, different size patients' and different reconstruction thickness. Unnecessary noise reduction and over-cleaning images resulting in inconsistent noise-level image data across slices or waxy/unnatural appearing processed images is avoided.

12 Claims, 6 Drawing Sheets

(56) References Cited

U.S. PATENT DOCUMENTS

| | | |
|---|---|---|
| 2014/0270053 A1 | 9/2014 | Larson |
| 2015/0201895 A1 | 7/2015 | Suzuki |
| 2015/0317777 A1 | 11/2015 | Koehler |
| 2017/0169564 A1* | 6/2017 | Hansen ................. G06F 19/321 |
| 2017/0178366 A1 | 6/2017 | Wang et al. |
| 2018/0033156 A1 | 2/2018 | Lee et al. |

OTHER PUBLICATIONS

Armando Manduca, "Projection space denoising with bilateral filtering and CT noise modeling for dose reduction in CT", Medical Physics, vol. 36, No. 11, Nov. 2009, p. 4911-4919.

Notification of Transmittal of the International Search Report and the Written Opinion of the International Searching Authority, or the Declaration dated Jul. 9, 2019 in connection with International Patent Application No. PCT/US2019/026042, 8 pages.

Bodelle et al. "Iterative Reconstruction Leads to Increased Subjective and Objective Image Quality in Cranial CT in Patients With Stroke", American Journal of Roentgenology, vol. 205, No. 3, Sep. 2015, pp. 618-622.

Zakaria et al. "Sinogram Concept Approach in Image Reconstruction Algorithm of a Computed Tomography System Using MATLAB", 2010 International Conference on Computer Applications and Industrial Electronics, Dec. 2010, pp. 500-505.

Geyer et al. "State of the Art: Iterative CT Reconstruction Techniques", Radiology, vol. 276, No. 2, Aug. 2015, pp. 339-357.

Notice of Allowance in connection with U.S. Appl. No. 16/374,490 dated Sep. 8, 2020, 8 pages.

Caraffa, Laurent, et al., "The Guided Bilateral Filter: When the Joint/Cross Bilateral Filter Becomes Robust," IEEE Transactions on Image Processing, 2015, 24 (4), pp. 1199-1208.

* cited by examiner

ADAPTIVE PROCESSING OF MEDICAL IMAGES TO REDUCE NOISE MAGNITUDE

PRIORITY CLAIM

This application claims priority to U.S. Provisional Patent Application No. 62/654,158 filed Apr. 6, 2018 and entitled PRE-FILTERED THREE-DIMENSIONAL BILATERAL FILTER REDUCTION OF CT IMAGE NOISE BY NOISE REDUCTION OF CT IMAGE USING PRE-FILTERED 3D BILATERAL FILTER. The content of the above-identified patent document(s) is incorporated herein by reference, together with the contents of any references cited either in the above-identified patent document(s) or herein.

TECHNICAL FIELD

The present application relates generally to computed tomography scan image noise and, more specifically, to reducing image noise from low radiation dose scanning.

BACKGROUND

Computed tomography (CT) scanning is a diagnostic imaging technique providing detailed representations of internal organs, bones, and soft tissue of the human body, in which cross-sectional data derived from a CT scan is reformatted in multiple planes to generate three-dimensional (3D) representations for human viewing. CT scanning is often used, for example, to determine the presence, size, and location of a cancer tumor or diagnose internal injuries and/or bleeding.

For CT imaging, there is a tradeoff between radiation dosage levels and image quality. Generally, higher radiation doses result in higher signal-to-noise ratio and higher resolution images with fewer artifacts, while lower doses lead to increased image noise and more artifacts and less-sharp images. In addition to ameliorating patient health concerns associated with high dose radiation scanning, reducing radiation dose for acquiring CT scans increases the tube life for the scanning machine—but increases noise. It would be desirable, therefore, to reduce the noise associated with low radiation dose scanning to produce high-quality CT images.

There are many different noise reduction methods for CT images, including iterative reconstruction (IR). Most provide several different modes affording different levels of demising, and a mode must be selected to denoise images. Especially in IR, an IR strength must be selected and set in a CT protocol, and unless a CT technologist manually changes the strength, the same IR strength is applied to patients of different (cross-sectional) size.

Even in an individual patient, the CT image noise magnitudes within scans are different depending on slices. In such a situation, if a single denoising mode or IR strength is used, a noisy slice may not be denoised enough while a less noisy slice could be over cleaned because of the fixed denoising strength.

Even in a patient and in a same slice location, the image noise levels are different depending on reconstruction thickness of CT images. In such a situation, if a single denoising mode or IR strength is used, a thin slice image may not be denoised enough while a thick slice image could be over-cleaned because of the fixed denoising strength.

SUMMARY

Each of a plurality of slices of medical image data is adaptively processed using a noise reduction mode selected according to a target noise magnitude for all slices to an estimated noise magnitude for the respective slice to obtain consistent processed images for all slices. Unnecessary noise reduction and over-cleaning images resulting in inconsistent noise-level image data across slices or waxy/unnatural appearing processed images are avoided.

Each of different size patients' medical image data is adaptively processed using a noise reduction mode selected according to a target noise magnitude for across different size of patient images to an estimated noise magnitude for the respective size of patients' image data to obtain consistent processed images for all size of patients' image data. Unnecessary noise reduction and over-cleaning images resulting in inconsistent noise-level image data across slices or waxy/unnatural appearing processed images are avoided.

Each of different slice thickness of medical image data is adaptively processed using a noise reduction mode selected according to a target noise magnitude for across different slice thickness of medical image data to an estimated noise magnitude for the respective slice thickness of image data to obtain consistent processed images for all slice thickness of images. Unnecessary noise reduction and over-cleaning images resulting in inconsistent noise-level image data across slices or waxy/unnatural appearing processed images are avoided.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; and the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

FIGS. 1 through 6F, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged data processing system connected to generate or receive, process, and display CT scan image data.

Figure 1:
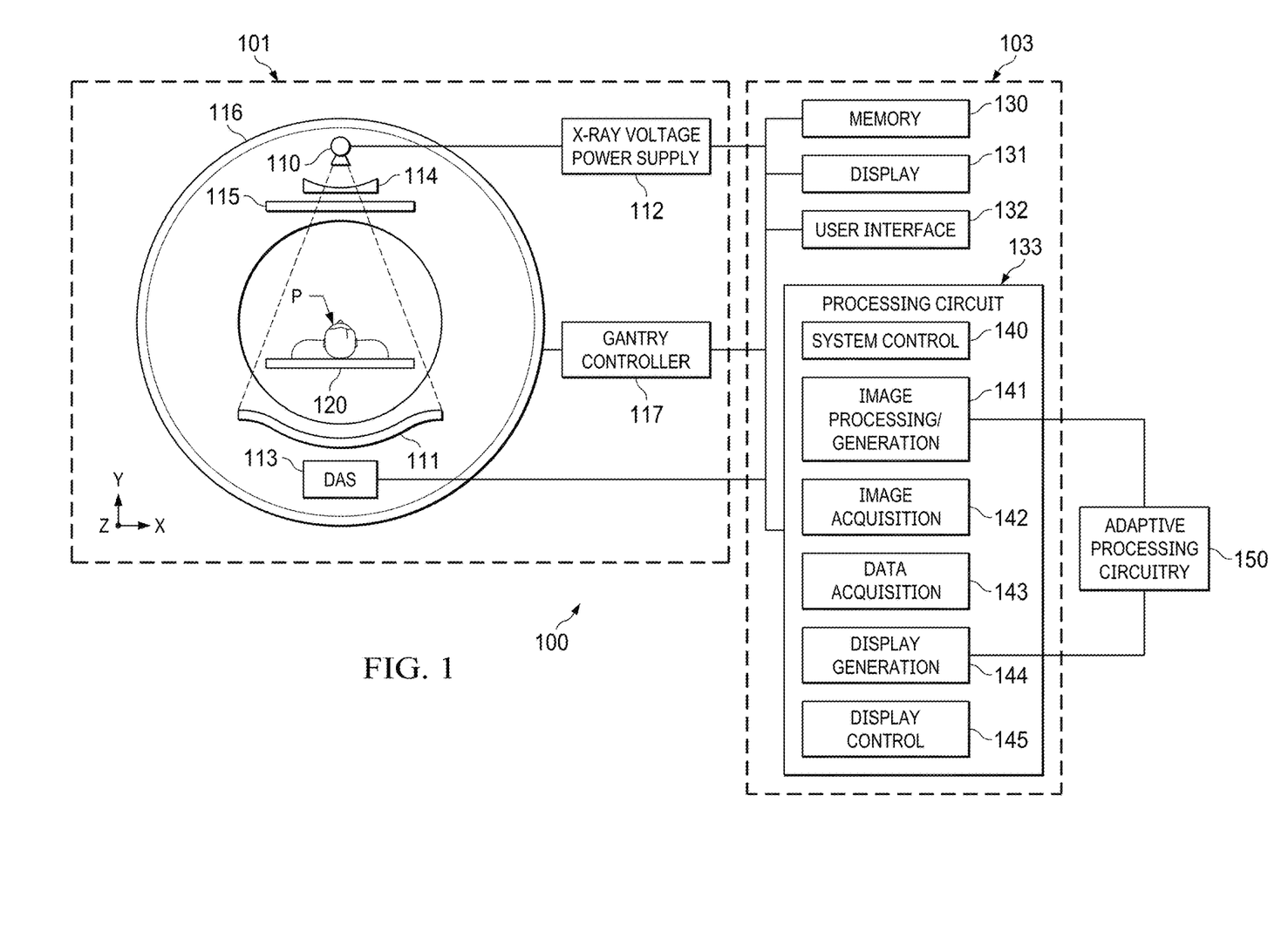
FIGS. 1 and 1A are diagrams of the overall configuration of a medical imaging and diagnosis system using adaptive processing to reduce noise magnitude according to embodiments of the present disclosure.
Figure 1A:
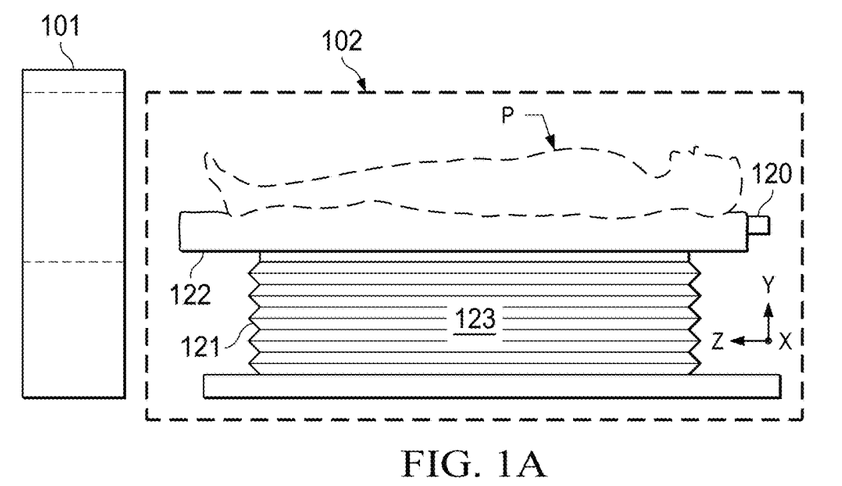

FIGS. 1 and 1A are diagrams of the overall configuration of a medical imaging and diagnosis system using adaptive processing to reduce noise magnitude according to embodiments of the present disclosure. FIG. 1 is in the nature of a schematic and/or block diagram, while FIG. 1A illustrates portions of FIG. 1 somewhat more pictorially. In the following description, an x-ray CT system is described as an example of the medical imaging and diagnosis system 100. However, the techniques of the present disclosure could be adapted to other systems.

The medical imaging and diagnosis system (x-ray CT system) 100 includes a gantry 101, a bed assembly 102, and a console 103. The gantry 101 is a device configured to acquire information on internal portions of a subject P to be examined or treated, in order to generate a medical image of those internal portions of the subject P. The bed 102 is a device on which the subject P is placed. The console 103 is connected and configured to control the entire medical imaging and diagnosis system 100, including the gantry 101 and the bed 102.

The gantry 101 includes an x-ray generator 110, an x-ray detector 111, an x-ray high-voltage power supply 112, a data acquisition system (DAS) 113, a wedge 114, a collimator 115, a rotating frame 116, and a controller 117. The x-ray generator 110 includes an x-ray tube (vacuum tube) that, for example, in response to the supply of high voltage from the x-ray high-voltage power supply 112, irradiates thermoelectrons from a cathode (or "filament") to an anode (or "target"). The x-ray detector 111 detects x-rays irradiated from the x-ray generator 110 that have passed through (or around) the subject P. The x-ray detector 111 outputs an electrical signal to the DAS 113 corresponding to the amount of the x-rays detected. The x-ray detector 111 includes, for example, a plurality of x-ray detection element arrays each including a plurality of x-ray detection elements are arranged in the channel direction along one circular arc around the focus of the x-ray tube within the x-ray generator 110. The x-ray detector 111 has a structure in which, for example, the x-ray detection element arrays, where the x-ray detection elements are arranged in the channel direction, are arrayed in a slice direction to generate a medical image of a cross-sectional portion of the subject P. The x-ray detector 111 may be, for example, an indirect-conversion detector that includes a grid, a scintillator array, and an optical sensor array. The scintillator array has a plurality of scintillators each formed of scintillation crystals that emit light with a number of photons corresponding to the incident x-ray amount. The grid of the x-ray detector 111 is arranged on a surface of the scintillator array on the side where x-rays are incident, and includes an x-ray shielding plate having the function of absorbing scattered x-rays. The optical sensor array has the function of converting x-rays into electric signals corresponding to the amount of light from the scintillator array. The optical sensor array includes, for example, an optical sensor such as a photomultiplier tube (PMT).

Alternatively, the x-ray detector 111 may be a direct-conversion detector having a semiconductor element that converts incident x-rays into electric signals.

The x-ray high-voltage power supply 112 is provided with electric circuits such as a transformer and a rectifier, and includes a high-voltage generator having the function of generating a high voltage to be applied to the x-ray generator 110, as well as an x-ray controller that controls the output voltage according to x-rays irradiated by the x-ray generator 110. The high-voltage generator 112 may be of transformer type or inverter type. The x-ray high-voltage power supply 112 may be arranged on the rotating frame 116 or on the side of a fixed frame (not illustrated) of the gantry 101, which fixed frame rotatably supports the rotating frame 116.

The DAS 113 includes at least an amplifier and an analog-to-digital (A/D) converter. The amplifier amplifies an electric signal output from each of the x-ray detection elements of the x-ray detector 111, while the A/D converter converts the electric signal into a digital signal. The DAS 113 generates detection data (pure raw data) that is sent to the console 103.

The wedge 114 (also sometimes called a "wedge filter" or a "bow-tie filter") is a filter for adjusting the dose of x-rays irradiated from the x-ray generator 110. Specifically, the wedge 114 attenuates x-rays irradiated from the x-ray generator 110 as the x-rays pass therethrough, such that the subject P is irradiated with the x-rays of a predetermined distribution. The wedge 114 is made of, for example, aluminum processed so as to have a predetermined target angle or a predetermined thickness.

The collimator 115 includes lead plates or the like for narrowing the irradiation range of the x-rays having passed through the wedge 114, forming a slit by a combination of a plurality of lead plates or the like.

The rotating frame 116 supports the x-ray generator 110 and the x-ray detector 111 arranged therein at positions facing each other. The rotating frame 116 is an annular frame that rotates the x-ray generator 110 and the x-ray detector 111 according to a signal from the controller 117. In addition to the x-ray generator 110 and the x-ray detector 111, the rotating frame 116 may also support the x-ray high-voltage power supply 112 and the DAS 113 arranged therein. With this structure, the rotating frame 116 performs imaging while the x-ray generator 110 and the x-ray detector 111 are rotated together integrally around the subject P at the center of rotation, irradiating the subject P with x-rays from different angles and detecting the x-rays that have passed through the subject P. The rotating frame 116 is provided with an annular opening to let the subject P resting on top plate 120 to enter and exit.

The rotating frame 116 may be provided with a transmitter having a light emitting diode (LED) to transmit detection data generated by the DAS 113 to a receiver via optical communication. The receiver has a photodiode provided in a non-rotating part of the gantry 101 such as, for example, the fixed frame (not shown). The detection data received by the receiver is sent to the console 103. The detection data need not necessarily transmitted via optical communication from the rotating frame 116 to the non-rotating part of the gantry 101, and any method can be employed as long as non-contact data transmission is implemented.

As illustrated in FIG. 1, the rotation axis of the rotating frame 116 is generally aligned in a direction parallel to the longitudinal direction of the top plate 120 of the bed assembly 102, which is defined as the z-axis direction of a Cartesian coordinate system. An axial direction perpendicular to the z-axis direction and horizontal to the floor surface is defined as the x-axis direction, while an axial direction perpendicular to the z-axis direction and vertical to the floor surface is defined as the y-axis direction.

The gantry controller 117 includes a processing circuit having a central processing unit (CPU) and the like, and driving mechanisms such as motor(s) and actuator(s). The gantry controller 117 has the function of controlling the operation of the gantry 101 and the bed 102 in response to an input signal from a user input interface attached to the console 103 or the gantry 101. Upon receipt of an input signal, for example, the gantry controller 117 controls the rotating frame 116 to rotate, controls the gantry 101 to tilt, or controls the top plate 120 within the bed assembly 102 to move. The gantry controller 117 may be located in the gantry 101 or may be located in the console 103. The gantry controller 117 tilts the gantry 101 by rotating the rotating frame 116 about an axis parallel to the x-axis direction based on tilt angle information provided through the user input interface attached to the gantry 101.

The bed assembly 102 is a device on which the subject P to be scanned is placed, and moves the subject P. The bed assembly 102 includes a base 121, the top plate 120, a support frame 122, and a bed driving device 123. The base 121 supports the support frame 122 (which includes the top plate 120) movably in the vertical direction (they direction indicated by the arrow in FIG. 1) in the frame of the bed assembly 102. The top plate 120 is a plate on which the subject P is placed. The support frame 122 supports the top plate 120 on its upper surface. The bed driving device 123 is a motor and/or actuator to move the top plate 120 on which the subject P is placed in the longitudinal (z) direction of the top plate 120 or in the vertical (y) direction (vertical direction with respect to the floor surface). The bed driving device 123 is driven in response to an input signal from the console 103, and moves the top plate 120 in one or more of the directions described above. In addition to the top plate 120, the bed driving device 123 may also move the support frame 122 in the longitudinal direction of the top plate 120. Since the bed driving device 123 is located inside the base 121, it is illustrated by broken lines in FIG. 1.

The console 103 includes a memory 130, a display 131, a user input interface 132, and processing circuitry 133. The memory 130 is implemented by, for example, a semiconductor memory element such as a random access memory (RAM) or a flash memory, a hard disk, an optical disk, or the like. The memory 130 stores, for example, raw detection data, projection data and/or reconstructed image data. The display 131 displays various types of information such as, for example, medical images (CT images) generated by the processing circuit 133, a graphical user interface (GUI) for displaying system information to and receiving various instructions from the operator, and the like. The display 131 is formed of, for example, a touch-screen liquid crystal display (LCD) or the like. The user input interface 132 receives various types of input from the operator, converting those input(s) into electric signal(s) that are outputs to the processing circuitry 133 and or the motors and/or actuators mentioned above. For example, the user input interface 132 receives, from the operator, collection conditions for collecting projection data, reconstruction conditions for reconstructing a CT image, image processing conditions for generating a post-processing image from the CT image, and the like. The user input interface 132 is realized by, for example, a mouse, trackball, trackpad, and/or touchscreen; a keyboard; dedicated switches and/or buttons; a joystick; or some combination thereof.

The processing circuitry 133 controls the operation of the entire medical imaging and diagnosis system 100 according to the electrical signal(s) input at the user input interface 132 and various electrical feedback and control signals. The processing circuitry 133 implements, for example, system control 140, image processing/generation 141, image acquisition 142, data acquisition 143, display generating 144, and display control 145. System control 140 controls various functions of the processing circuitry 133 based on input(s) received from the operator through the user input interface 132. In some embodiments, image processing/generation 141 performs preprocessing, reconstruction, and image processing. The preprocessing operates on data output from the DAS 113 by processing such as logarithmic conversion, offset correction, inter-channel sensitivity correction, beam hardening correction, and the like. Note that data before preprocessing and data after preprocessing may sometimes be collectively referred to as "projection data." Reconstruction generates CT image data by reconstructing the projection data generated by the preprocessing function using a filtered back projection method, a successive approximation reconstruction method, or the like. Image processing converts the CT image data generated by the reconstruction function into three-dimensional image data or tomographic image data of an arbitrary cross section by a known method based on an input received from the operator through the user input interface 132. Image acquisition 142 acquires medical image data of a scan. More specifically, the image acquisition 142 acquires medical image data selected from medical image data (or "medical image") generated by the image processing/generation 141 based on a selection operation by the operator.

Based on medical image data acquired by image acquisition 142, data acquisition 143 acquires pixel value data contained in the medical image data. The pixel value data is acquired with respect to each region set by the operator. Display generation 144 generates display information based on the pixel value data. The display information is generated with respect to each region set by the operator as described above. Display control 145 causes displays on the display 131 of a CT image (medical image) based on CT image data acquired by image acquisition 142. The display conditions of the medical image are set according to an input signal provided by the operator through the user input interface 132. Display control 145 also displays the display information in a corresponding area of medical image data (representative image), and displays the display information in a predetermined display range, processing the display information in various display modes according to the conditions set by the operator.

In addition to the above-described functions, the processing circuitry 133 may have, for example, a scan control function that controls the driving of each part of the gantry 101 and/or the bed assembly 102 according to various conditions of scanning (imaging of the subject) provided through the user input interface 132.

In the above description of the overall configuration of the medical imaging and diagnosis system 100 of one embodiment, system control 140, image processing/generation 141, image acquisition 142, data acquisition 143, display generation 144 and display control 145 may optionally be implemented by computer executable programs, which are stored in a memory circuit such as, for example, the memory 130 and read from the memory circuit and executed by the processing circuitry 133 to realize the corresponding function described herein. In other words, having read the programs, the processing circuitry 133 implements the functions for the modules illustrated in FIG. 1. However, although the processing circuitry 133 may be implemented by a single programmable processor, it is not so limited. Instead, the processing circuitry 133 may be formed of a combination of a plurality of independent processors, each of which executes a program to realize corresponding one of the functions. Alternatively, dedicated hardware circuitry (or partially programmable circuitry) may be implemented, in one integrated circuit or in a plurality of integrated circuits, for each module depicts or for some combination of such modules. In addition, the programs each corresponding to one of the functions are described as being stored in a single memory circuit (the memory 130), but can instead be stored in a plurality of memory circuits arranged in a distributed manner, and the processing circuit may read each of the programs from each of the memory circuits.

In embodiments according to the present disclosure, adaptive processing circuitry 150 may operate as part of, prior to, or subsequent to image processing/generation 141. In general, the adaptive processing circuitry 150 may operate on low-dose CT scans in digital imaging and communications in medicine (DICOM) format or other image format including RAW image format, and sends the processed image data to a picture archiving and communication system (PACS) or other system without changing the radiology workflow. Adaptive processing circuitry 150 may therefore be implemented in a server separate from console 103, and may in fact be remote from both bed assembly 102 and console 103. In such cases, adaptive processing circuitry 150 may receiving scan data electronically from either bed assembly 102 or console 103, and returns processed data to console 103 for further processing and/or display. In some embodiments, adaptive processing circuitry 150 may receive scan data from multiple imaging centers with scanner from different vendors, and processes noisy CT scans from such scanners regardless of the vendor.

Whereas iterative reconstruction (IR) processing can result in noise-level image data depending on input image data's noise level or waxy/unnatural images, the adaptive processing circuitry 150 operates to reduce noise to make output images more consistent across "slices" (cross-sectional medical images for different regions) while avoiding unnecessary denoising or over-cleaned images. Processed medical images produced by the adaptive processing circuitry 150 look natural, but have reduced blur.

Figure 2:
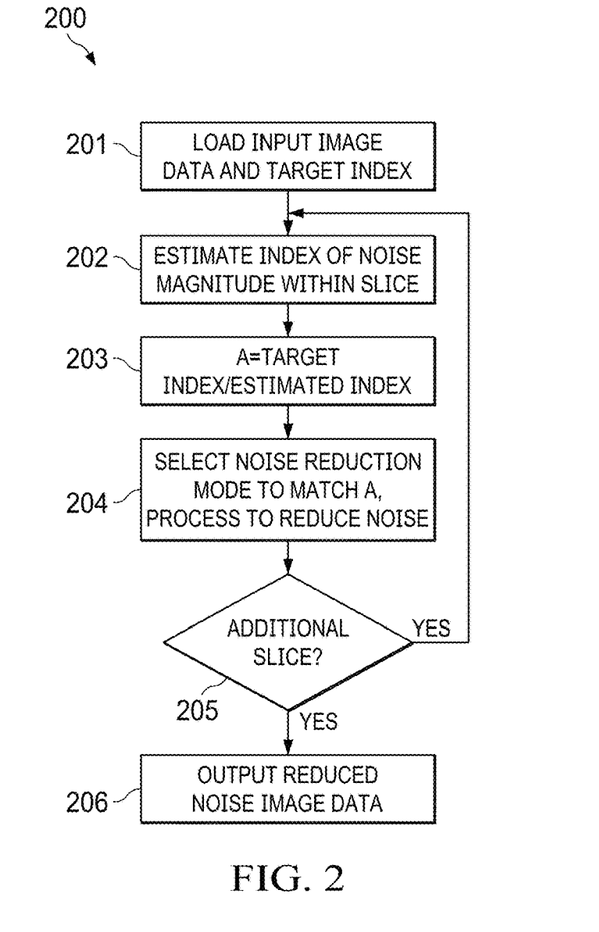
FIG. 2 is a high level flowchart of adaptive processing of medical image data according to embodiments of the present disclosure.

FIG. 2 is a high level flowchart of adaptive processing of medical image data according to embodiments of the present disclosure. The process 200 begins with loading an input image data and a target index for noise magnitude (step 201). The index of noise magnitude (for example, additive white Gaussian noise) within a slice of the medical image data is estimated (step 202), for example based on standard deviation in or related to signal-to-noise ratio (SNR), peak-to-signal noise ratio (PSNR), root mean square error (RMSE), or other known noise estimation techniques. The noise reduction ratio A, which is the ratio of the target noise magnitude index to the estimated noise magnitude index, is then determined for the current slice (step 203). A noise reduction mode, which can achieve the noise reduction ratio closest to A, is then selected and the slice is processed using the selected noise reduction mode (step 204). If additional slices remain within the image data loaded (step 205), another iteration is performed for the next slice. Otherwise, the reduced noise image data produced by the adaptive processing is output (step 206) for storage, display, and/or further processing.

In step 201, the input image data can be also sinograms, which are projected images in CT, instead of reconstructed data. In the case of sinograms, the noise reduction methods used in 204 include reconstruction such as iterative reconstructions. Or, the reconstruction can be done as a preprocessing between steps 201 and 202.

In step 201, instead of using target index, other index such as effective mAs, which is correlated to image noise, can be used.

Figure 3:
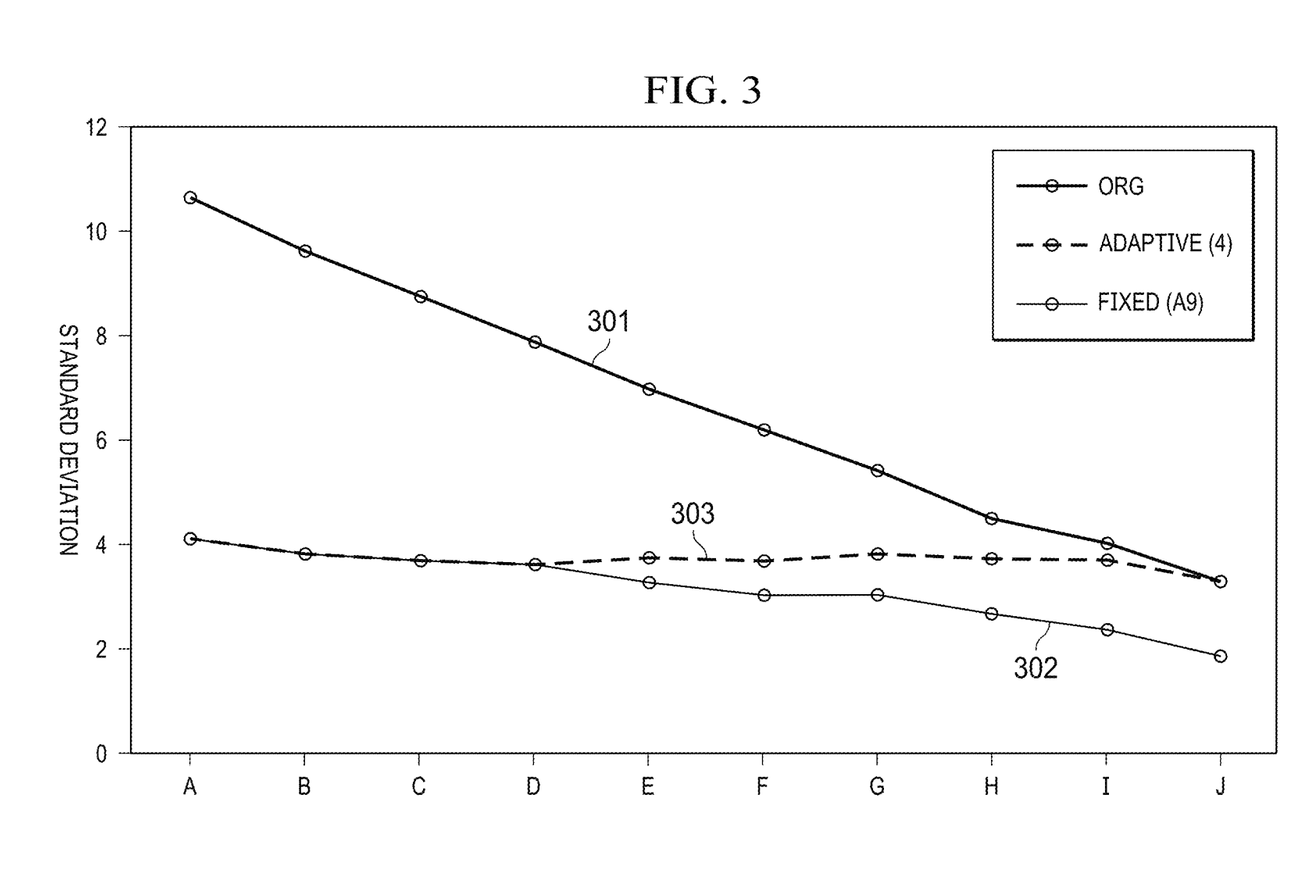
FIG. 3 comparatively illustrates adaptive processing based on standard deviations of noise magnitude in accordance with FIG. 2 and fixed mode processing of image data having different noise levels.

FIG. 3 comparatively illustrates adaptive processing based on standard deviations of noise magnitude in accordance with FIG. 2 and fixed mode processing of image data having different noise levels. Original data 301 for image data A through J, each of the same image data but with a different one of 10 different noise levels (based on standard deviation), are processed separately by adaptive processing and by fixed processing. Image data A has the largest amount of noise, while image data J has the least and, as apparent from the plot, the noise level decreases by a relatively consistent amount within the intervening images. Processed data 302 for fixed strength processing significantly reduces noise in image data A through D. However, the fixed processing also reduces noise in image data H through J, where less noise reduction is necessary to avoid waxy/unnatural appearing while retaining a natural-appearing image.

Processed data 303 for adaptive processing according to FIG. 2 produces noise reduction comparable to that of the fixed processing for image data A through D. However, for image data I and J, for example, less noise reduction occurs than for the fixed processing because the amount of noise reduction necessary is less. Thus, across the range of noise levels, noise reduction is matched to the amount required to reduce blurriness without compromising the accuracy of the resulting image.

Figure 4A:
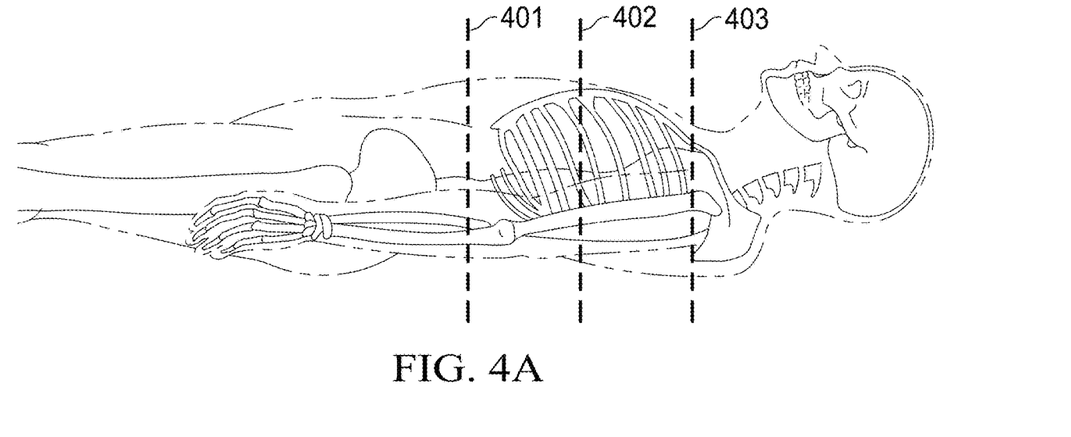
FIGS. 4A through 4G depict exemplary results of applying adaptive processing in accordance with embodiments of the present disclosure to image data scanned at different locations of a single patient.
Figure 4B:
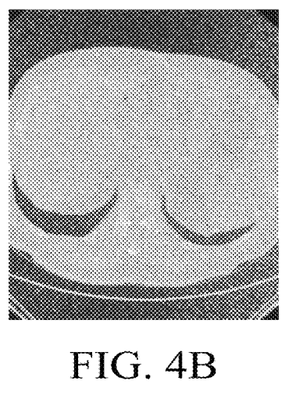
Figure 4C:
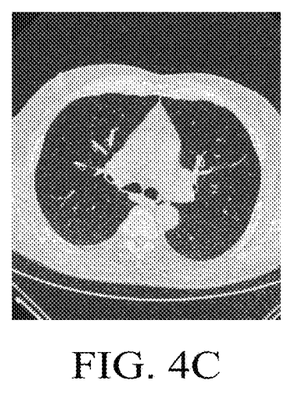
Figure 4D:
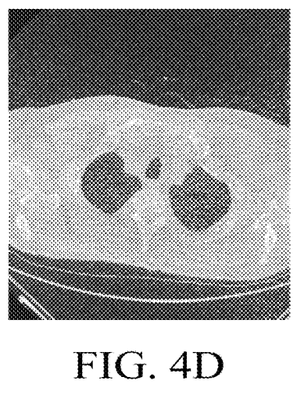
Figure 4E:
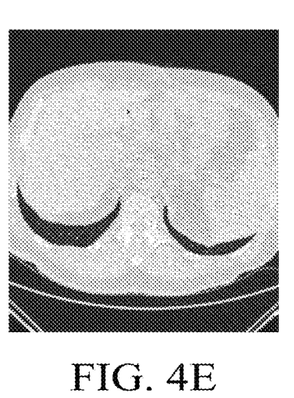
Figure 4F:
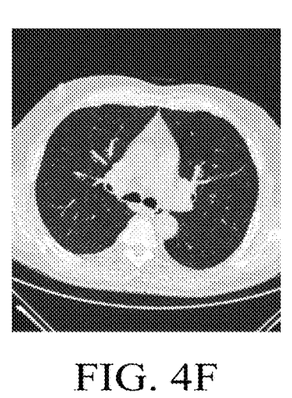
Figure 4G:
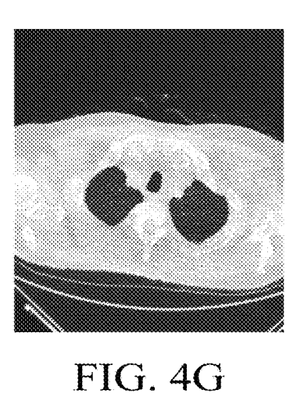

FIGS. 4A through 4G depict exemplary results of applying adaptive processing in accordance with embodiments of the present disclosure to image data scanned at different locations of a single patient. FIG. 4A depicts the locations 401, 402 and 403 of scans on a patient's body. FIG. 4B is an image based on the original scan data from location 401; FIG. 4C is an image based on the original scan data from location 402; and FIG. 4D is an image based on the original scan data from location 403. The scan data for locations 401 and 403 are noisier than the scan data from location 402. FIG. 4E is an image for the scan data from location 401 after application of adaptive processing as described above in connection with FIG. 2. Similarly, FIG. 4F is an image for the scan data from location 402 and FIG. 4G is an image for the scan data from location 403, both after application of adaptive processing as described above in connection with FIG. 2. FIGS. 4E, 4F and 4G have consistent noise magnitude—that is, less variation in the noise magnitude, despite the variation in noise within the unprocessed scan data. FIG. 4F has not been overcleaned of noise, and retains realistic appearance.

Figure 5A:
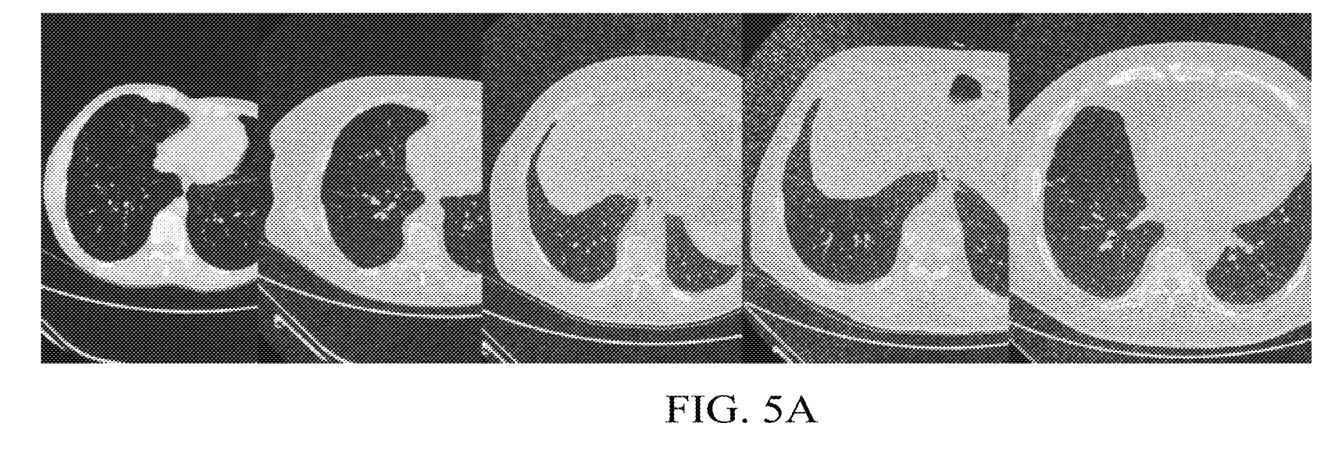
FIGS. 5A and 5B depict exemplary results of applying adaptive processing in accordance with embodiments of the present disclosure to image data scanned for patients of different sizes.
Figure 5B:
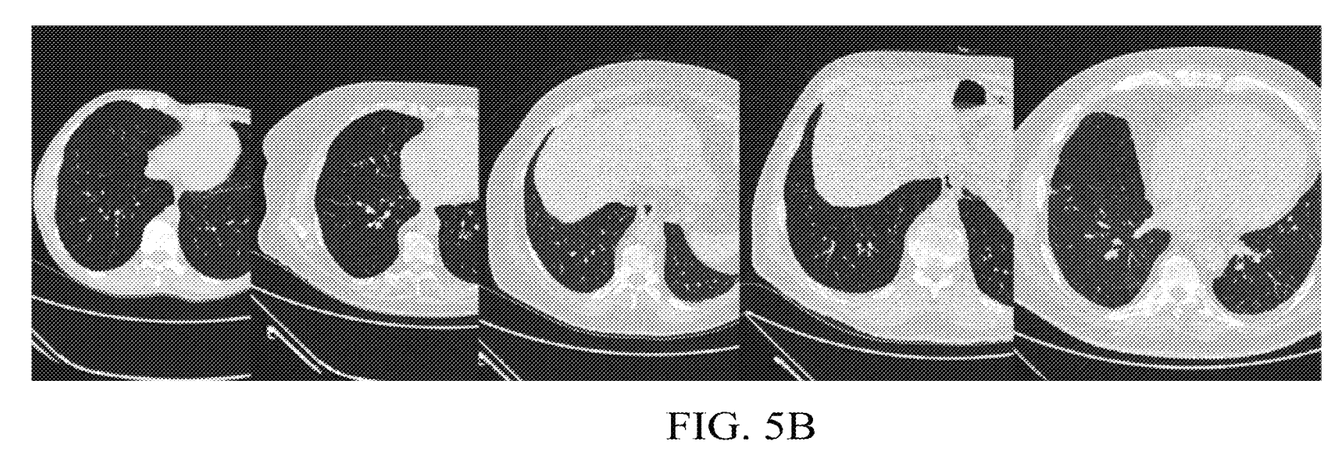

FIGS. 5A and 5B depict exemplary results of applying adaptive processing in accordance with embodiments of the present disclosure to image data scanned for patients of different sizes. FIG. 5A includes images based on the original (unprocessed) scan data. As evident from FIG. 5A, the cross-sectional dimensions of the patient features being scanned increase from left to right, and the noise magnitude likewise increases from left to right (with the leftmost image being least noisy and the rightmost image being noisiest). FIG. 5B includes images for the scan data corresponding to FIG. 5A after application of adaptive processing as described above in connection with FIG. 2. As with FIGS. 4E, 4F, and 4G, the images in FIG. 5B have consistent noise levels with less variation despite substantial disparity in the noise within the different original scans.

Figure 6A:
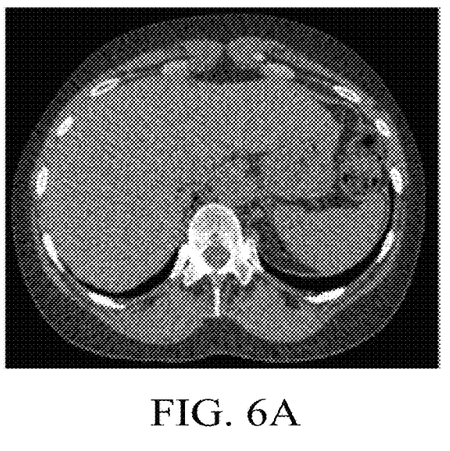
FIGS. 6A through 6F depict exemplary results of applying adaptive processing in accordance with embodiments of the present disclosure to image data scanned with different slice thickness.
Figure 6B:
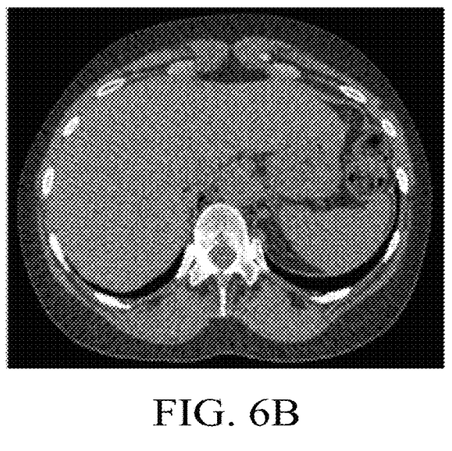
Figure 6C:
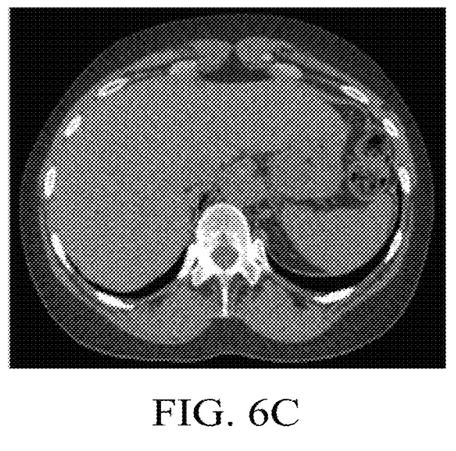
Figure 6D:
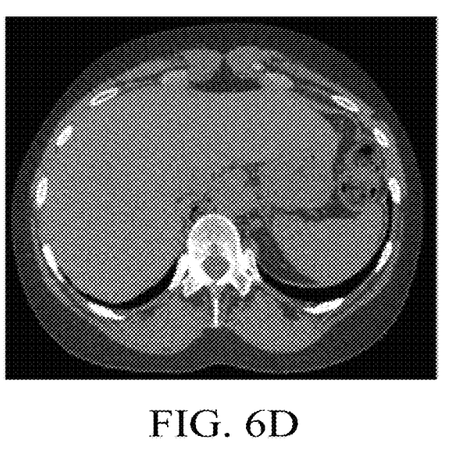
Figure 6E:
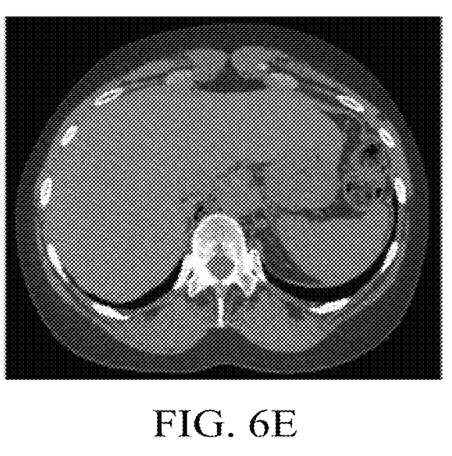
Figure 6F:
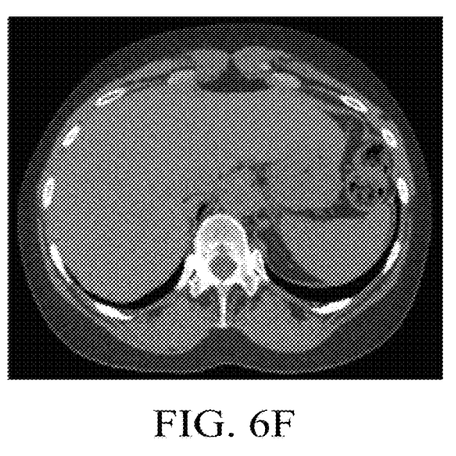

FIGS. 6A through 6F depict exemplary results of applying adaptive processing in accordance with embodiments of the present disclosure to image data scanned with different slice thickness. FIG. 6A is based on a reconstruction thickness of 0.625 millimeter (mm); FIG. 6B is based on a reconstruction thickness of 1.25 mm; and FIG. 6C is based on a reconstruction thickness of 2.50 mm. As apparent, FIG. 6A is noisier than FIGS. 6B and 6C, while FIG. 6C is less noisy than FIGS. 6A and 6B. FIGS. 6D, 6E and 6F correspond to FIGS. 6A, 6B and 6C, respectively, after application of adaptive processing as described above in connection with FIG. 2. As apparent, the noise levels in FIGS. 6D, 6E and 6F are more consistent and have less variation than would result from fixed processing.

REFERENCES

Geyer. L., Schoepf, U. J., et al. State of the Art: Iterative CT Reconstruction Techniques, Radiology, 2015; 276:339-357.

Bodelle, B., Wichmann, J. L., et al. Iterative Reconstruction Leads to Increased Subjective and Objective Image Quality in Cranial CT in Patients With Stroke. AJR:2015; 205:618-622.

Zakaria, Z., Jaafar, N. H., et al. Sinogram Concept Approach in Image Reconstruction Algorithm of a Computed Tomography System Using MATLAB. ICCAIE 2010, Kuala Lumpur, Malasia.

Although the present disclosure has been described with exemplary embodiments, various changes and modifications may be suggested to one skilled in the art. It is intended that the present disclosure encompass such changes and modifications as fall within the scope of the appended claims.

What is claimed is:

1. An image processing method, comprising:
storing medical image data in a memory coupled to processing circuitry; and
for a plurality of slices of the medical image data having varying amounts of noise ranging from a most noisy of the plurality of slices to a least noisy of the plurality of slices, for each respective one of the plurality of slices:
estimating a noise magnitude within the respective slice,
selecting one of a plurality of noise reduction modes to be used for processing the respective slice based on an amount of noise reduction corresponding to reduction of the estimated noise magnitude for the respective slice without compromising accuracy in a processed image for the respective slice, and wherein the selected one of the plurality of noise reduction modes to be used for processing the respective slice is selected independent of a noise reduction mode selected for others of the plurality of slices,
processing the respective slice using the selected one of the plurality of noise reduction modes, and
storing the processed image corresponding to the processed respective slice,
wherein a plurality of processed images is obtained corresponding to the plurality of slices, and wherein the plurality of processed images have more consistent noise magnitude(s) than the plurality of slices.

2. The method according to claim 1, wherein a first noise reduction mode is selected for a first of the plurality of slices and a second noise reduction mode is selected for a second of the plurality of slices.

3. The method according to claim 2, wherein the processing for each the first and second slices is based on a magnitude of noise within the first and second slices.

4. The method according to claim 1, wherein two or more of the plurality of slices of medical image data are different patients' image data and wherein the plurality of processed images have more consistent noise magnitude across the different patients' image data.

5. The method according to claim 1, wherein two or more of the plurality of slices of medical image data of a patient acquired in different time and wherein the plurality of processed images have more consistent noise magnitude across the plurality of slices of medical image data of a patient acquired in different time.

6. The method according to claim 1, wherein the plurality of slices of medical image data correspond to different reconstruction thicknesses and wherein the plurality of processed images have more consistent noise magnitude across the different reconstruction thicknesses.

7. An image processing system, comprising:
memory configured to store medical image data; and
processing circuitry coupled to the memory and configured to receive the stored medical image data, the processing circuitry configured, for a plurality of slices of the medical image data having varying amounts of noise ranging from a most noisy of the plurality of slices, to a least noisy of the plurality of slices, for each respective one of the plurality of slices:
estimate a noise magnitude within the respective slice,
select one of a plurality of noise reduction modes to be used for processing the respective slice based on an amount of noise reduction corresponding to reduction of the estimated noise magnitude for the respective slice without compromising accuracy in a processed image for the respective slice, and wherein the selected one of the plurality of noise reduction modes to be used for processing the respective slice is selected independent of a noise reduction mode selected for others of the plurality of slices,
process the respective slice using the selected one of the plurality of noise reduction modes,
store the processed image corresponding to the processed respective slice,
wherein a plurality of processed images is obtained corresponding to the plurality of slices, and wherein the plurality of processed images have more consistent noise magnitude(s) than the plurality of slices.

8. The system according to claim 7, wherein a first noise reduction mode is selected for a first of the plurality of slices and a second noise reduction mode is selected for a second of the plurality of slices.

9. The system according to claim 8, wherein the processing circuitry is configured to process each the first and second slices based on a magnitude of noise within the first and second slices.

10. The system according to claim 7, wherein two or more of the plurality of slices of medical image data are different patients' image data and wherein the plurality of processed images have more consistent noise magnitude across the different patients' image data.

11. The system according to claim 7, wherein two or more of the plurality of slices of medical image data of a patient acquired in different time and wherein the plurality of processed images have more consistent noise magnitude across the plurality of slices of medical image data of a patient acquired in different time.

12. The system according to claim 7, wherein the plurality of slices of medical image data correspond to different reconstruction thicknesses and wherein the plurality of processed images have more consistent noise magnitude across the different reconstruction thicknesses.

\* \* \* \* \*